United States Patent [19]

Benedict

[11] 4,256,730

[45] Mar. 17, 1981

[54] ORAL COMPOSITIONS

[75] Inventor: James J. Benedict, Cincinnati, Ohio

[73] Assignee: The Procter & Gamble Company, Cincinnati, Ohio

[21] Appl. No.: 936,452

[22] Filed: Aug. 24, 1978

[51] Int. Cl.$^3$ .......................... A61K 7/16; A61K 7/18
[52] U.S. Cl. ........................................ 424/52; 424/49; 424/53; 424/54; 424/56; 424/57; 426/548
[58] Field of Search ................................ 424/49–58; 426/548

[56] References Cited

U.S. PATENT DOCUMENTS 3,689,486   9/1972   Clauss et al. ............................. 544/2
3,932,606   1/1976   Barth et al. ............................. 424/52

OTHER PUBLICATIONS

Clauss and Jensen, Angewandte Chemie, vol. 12, No. 11, pp. 869–942, Nov. 1973, "Oxathiazinone Dioxide-A New Group of Sweetening Agents".

Primary Examiner—Shep K. Rose
Attorney, Agent, or Firm—Douglas C. Mohl; John V. Gorman; Richard C. Witte

[57] ABSTRACT

Oral compositions which contain as a sweetening agent 6-methyloxathiazinone dioxide or an alkali metal or alkaline earth salt thereof in an amount of from about 0.05% to about 0.80%.

10 Claims, No Drawings

ORAL COMPOSITIONS

TECHNICAL FIELD

The present invention relates to oral compositions which contain 6-methyloxathiazinone dioxide or an alkali metal or alkaline earth salt thereof as a sweetening agent.

In recent years a considerable amount of work has been conducted in the oral composition area in an effort to develop compositions having a high degree of consumer acceptance. One of the more important factors related to consumer acceptance is product taste, which is determined to a large extent by flavor and sweetness characteristics. Sweetness is generally imparted to oral compositions by the use of artificial sweeteners. The use of artificial sweeteners is advantageous in oral compositions as they are non-cariogenic. This noncariogenicity apparently arises from the fact that these artificial sweeteners are not metabolized by oral bacteria to form acids in the mouth, said acids being the primary cause of dental caries.

Heretofore, the synthetic sweeteners of choice for use in oral compositions have been the cyclamates, which are not now permissible ingredients in oral products, and the saccharin compounds, which are currently being investigated by the government for possible restriction. Although the saccharin compounds are still widely used, they possess sweetness characteristics which may leave a lingering bitter aftertaste perceived by some users.

While saccharin and the cyclamates are the most common of the artificial sweetening agents, numerous other artificial sweetening agents are known in the art. Examples include various dihydrochalcones having sugar substituents (glyconic dihydrochalcones), 5-(3-hydroxyphenoxy)-1H-tetrazole, [6-(trifluoromethyl)-tryptophane], dipeptide sweetening agents, monoammonium glycyrrhizinate, p-ethoxyphenylurea, d,1-tryptophan, p-anisylurea, d-tryptophan, amino acetic acid and 3,4-dihydro-1,2,3-orathizin-4-one as disclosed in U.S. Pat. No. 3,932,606, Jan. 13, 1976 to Barth et al.

While all of the above compounds possess sweetness characteristics, not every sweetening agent is suitable for use in oral compositions such as toothpastes and mouthwashes. The primary concern in formulating a toothpaste or a mouthwash is to achieve a product that is effective for its intended use. Toothpastes, mouthwashes and similar oral compositions are complex compositions which must be effective, safe and have consumer acceptability. In formulating such compositions, numerous unpredictable problems are frequently encountered. These problems are often associated with the sweetening agent which must be compatible with the rest of the base composition, safe for use in the oral cavity, and impart desirable sweetness characteristics. Not only is it imperative that the sweetening agent meet the above criteria, but in addition, it must be readily available at a price which is not eceonomically prohibitive for the use intended. It is evident that the discovery of novel oral compositions having all these desirable and necessary characteristics represents a significant advance in the oral composition art.

The present applicant has discovered that 6-methyloxathiazinone dioxide and its alkali metal and alkaline earth salts not only provide a sweeter oral product than similar compounds such as that described in the aforementioned 3,932,606 patent but also is more suitable for use in oral compositions for reasons of safety and compatibility.

BACKGROUND ART 6-methyloxathiazinone dioxide is known in the art. It has been described as an artificial sweetening agent possessing a sweetness of about 130 times that of sucrose when tested as the sodium or potassium salt. (Clauss and Jensen, Angewandte Chemie, "Oxathiazinone Dioxide—A new Group of Sweetening Agents," Vol. 12, No. 11, pp. 869-942, November, 1973.) The compound is also described in U.S. Pat. No. 3,689,486, Sept. 5, 1972 to Clauss et al.

It is a primary object of the present invention to provide novel oral compositions having desirable sweetness characteristics imparted to them by 6-methyloxathiazinone dioxide and its salts.

DISCLOSURE OF THE INVENTION

The present invention resides in the discovery that oral compositions which contain from about 0.05% to about 0.8%, preferably from about 0.1% to about 0.6% of 6-methyloxathiazinone dioxide or a salt thereof as a sweetening agent possess highly desirable sweetness characteristics with no undesirable aftertaste. In addition to imparting highly desirable sweetness characteristics to said oral compositions, 6-methyloxathiazinone dioxide has been found to be surprisingly compatible with other components of such compositions, resulting in a stable, desirable composition.

As used herein, the term "oral composition" means a product, which in the ordinary course of usage, is not intentionally ingested, but is retained in the oral cavity for a time sufficient to contact substantially all of the dental surfaces. Preferred compositions for purposes of the present invention include toothpastes, toothpowders, mouthwashes, mouthsprays and the like.

DETAILED DESCRIPTION OF THE INVENTION

More specifically, it has been discovered that highly desirable sweetness characteristics are imparted to certain oral compositions such as dentifrices, mouthwashes and the like which contain from about 0.05% to about 0.8% by weight of 6-methyloxathiazinone dioxide or an alkali metal or alkaline earth salt thereof.

Preferably, the oral compositions within the scope of the present invention which contain from about 0.3% to about 0.6% and more preferred for use in dentifrice compositions, with an amount of from about 0.075% to about 0.15% being most preferred for mouthwash compositions. The most preferred salt is the potassium salt.

Not only does the present invention reside in the discovery that 6-methyloxathiazinone dioxide and its alkali metals and alkaline earth salts can be utilized in oral compositions to give a compatible product having a highly desirable sweetness characteristics, but even more surprising is the discovery that the stability of such a product is superior to a product made with analogous materials.

The structure of 6-methyloxathiazinone dioxide is

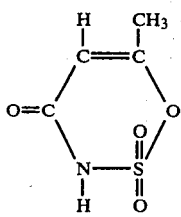

PREFERRED COMPOSITIONS

A typical dentifrice composition falling within the scope of the present invention contains one or more abrasive polishing materials, sudsing agents, flavor and sweetening agents. In addition, toothpastes generally contain humectants and binders. Optional ingredients such as water-soluble fluorides and antibacterials may be added. Other ingredients such as preservatives, buffers and coloring agents may also be added to add to the desirability of the composition.

More particularly, a toothpaste composition falling within the scope of the present invention consists of:
(A) from about 0.05% to about 0.80% of 6-methyloxathiazinone dioxide or an alkali metal or alkaline earth salt thereof;
(B) from about 0.5% to about 95% by weight of an abrasive material;
(C) from about 0.5% to about 5.0% of a sudsing agent;
(D) from about 0.1% to about 5.0% of a binder material;
(E) up to about 50% of a humectant material;
(F) from about 0% to about 1.0% of a water-soluble fluorine-containing compound; and
(G) balance, water and minors.

The preferred toothpaste compositions of the present invention contain the potassium salt of 6-methyloxathiazinone dioxide as the sole sweetening agent in an amount of from about 0.3% to about 0.6%.

6-methyloxathiazinone dioxide is well known and can be made in accordance with the procedure disclosed in U.S. Pat. No. 3,689,486 incorporated herein by reference.

Toothpaste compositions typically contain sudsing agents in an amount of from about 0.5% to about 5.0%. Suitable sudsing agents for use in the dentifrices of this invention are those which yield substantial levels of foam and which are otherwise acceptable for use in the oral cavity. Examples of suitable sudsing agents include the water-soluble salts of alkyl sulfate having from 10 to 18 carbon atoms, such as sodium lauryl sulfate; water-soluble salts of sulfonated monoglycerides, such as sodium coconut monoglyceride sulfonate; water-soluble salts of fatty acid amides of taurine, such as sodium N-methyl-N-palmitoyl tauride; water-soluble salts of fatty acid esters of isethionate; and substantially saturated aliphatic acyl amides of saturated aliphatic monoaminocarboxylic acid having 2 to 6 carbon atoms and in which the acyl radical contains 12 to 16 carbon atoms, such as sodium N-lauryl sarcosinate. Certain nonionic sudsing agents such as sorbitan monooleate polyoxyethylene are also suitable. Mixtures of two or more sudsing agents can also be used. A sudsing agent selected from the group consisting of sodium lauryl sulfate, sodium coconut monoglyceride sulfonate, and mixtures thereof is most preferred.

The abrasive polishing material contemplated for use in the present invention can be any material which does not excessively abrade dentin. These include, for example, calcium carbonate, dicalcium orthophosphate dihydrate, calcium pyrophosphate, tricalcium phosphate, calcium polymetaphosphate, insoluble sodium polymetaphosphate, hydrated alumina, and resinous abrasive materials such as particulate condensation products of urea and formaldehyde, and others such as disclosed by Cooley et al in U.S. Pat. No. 3,070,510 granted Dec. 25, 1962. Silica xerogels as disclosed in U.S. Pat. No. 3,538,230 to Pader et al on Nov. 3, 1970 can also be used. Synthetic amorphous silicas such as silica aerogels and pyrogenic silicas can also be used, preferably in combination with other abrasive materials. Still other abrasive materials include zirconium silicate and mixtures thereof with other cleaning and polishing agents as set forth in U.S. Pat. No. 3,450,813 to Muhler which issued on June 17, 1969. These patents are incorporated herein by reference.

Preferred abrasives for use in the present invention are those selected from the group consisting of calcium pyrophosphate, silica xerogels, silica aerogels and mixtures thereof.

The total amount of abrasive materials in the dentifrice embodiments of the present invention can range from about 0.5% to about 95% by weight of the dentifrice. Preferably, amounts of from about 10% to about 60% by weight are used.

In toothpastes, it is desirable to employ binders such as hydroxyethyl cellulose and water-soluble salts of cellulosic ethers including sodium carboxymethyl cellulose and sodium carboxymethyl hydroxyethyl cellulose; or natural gums including gum karaya, gum arabic, xantham gum and gum tragacanth. Seaweed derivatives such as Irish moss and aliginates can also be used. Colloidal magnesium aluminum silicate, hydrophobic clays such as bentonite, or finely divided silica can be used as part of the binding agent to improve the texture of the product. Other suitable compounds include high molecular weight carboxyvinyl polymers such as Carbopol 940 supplied by the B. F. Goodrich Chemical Company. Binding agents selected from the group consisting of sodium carboxymethyl cellulose, magnesium aluminum silicate, hydroxyethyl cellulose, Irish moss, xantham gum and mixtures thereof are most preferred, in amounts of from about 0.1% to about 5.0%.

It is also desirable to include humectants in toothpastes. Preferred humectants include glycerine, sorbital and other edible polyhydric alcohols and mixtures thereof. These materials can comprise up to about 50% of the toothpaste composition.

In addition to the above ingredients, toothpastes of the present invention may contain oral health agents. Examples of such compounds include fluorine-containing compounds such as stannous fluoride, sodium fluoride, lithium fluoride, indium fluoride, potassium fluoride, ammonium fluoride, sodium fluorostannite, stannous chlorofluoride, sodium monofluorophosphate, sodium hexafluoroantimonate, and anticalculus agents such as ethane-1-hydroxy-1, 1-diphosphonic acid (EHDP) and others as disclosed in U.S. Pat. No. 3,959,458, May 25, 1976 to Agricola et al. Preferred oral health agents for use in the present invention are those selected from the group consisting of sodium fluoride and stannous fluoride. Such compounds are generally present in amounts of from about 0.01% to about 1.0%.

The toothpaste compositions of the present invention may also contain various minor ingredients including water and/or ethyl alcohol, coloring agents, colored particles, preservatives, buffering agents, flavoring agents and antibacterials. These minor ingredients in total can be present in amounts of up to about 50%.

Examples of suitable flavoring agents include heliotropyl nitrile, paramethoxy cinnamaldehyde, wintergreen oil (methyl salicylate), oil of peppermint, oil of spearmint, and the like, and mixtures thereof. Generally, flavoring agents are present in amounts of from about 0.001% to about 1.0%.

Examples of suitable antibacterial compositions for use in the dentifrices of the present invention include chlorhexidine, cetyl pyridinium chloride, and domiphen bromide. Said compositions can be utilized in amounts of from about 0.01% to about 0.10%.

Other preferred compositions within the scope of the present invention include mouthwashes and similar compositions such as concentrated mouthsprays. Mouthwashes generally comprise a water/ethyl alcohol solution and flavoring and sweetening materials. The alcohol provides an antibacterial effect and also solubilizes the flavoring materials.

In addition, mouthwashes may contain as optional ingredients a variety of oral health agents, additional antibacterial agents, emulsifiers and surfactants, humectants, flavoring and coloring agents.

More specifically, mouthwashes contemplated for use in the present invention consist of:
(A) from about 0.05% to about 0.8% of an alkali metal salt of 6-methyloxathiazinone dioxide or an
(B) from about 5% to about 60% of ethyl alcohol;
(C) from about 5% to about 20% of a humectant; and
(D) balance, water and minors.

Most preferably, the mouthwash compositions of the present invention contain from about 0.075% to about 0.15% of the potassium salt of 6-methyloxathiazinone dioxide.

Examples of suitable humectants for use in the mouthwashes contemplated for use in the present invention include glycerine, sorbitol, and other edible polyhydric alcohols or mixtures thereof. Amounts of from about 5% to about 20% are preferred. For the purposes of the present invention, glycerine is most preferred.

In addition to the above ingredients, mouthwashes and similar compositions falling within the scope of the present invention may also contain as minor ingredients oral health agents including fluoride compounds such as sodium and indium fluoride, and anticalculus agents such as ethane-1-hydroxy-1, 1-diphosphonic acid (EHDP), and similar compounds as disclosed in U.S. Pat. No. 3,595,458, Agricola et al, previously incorporated herein by reference. Other minor ingredients such as flavor and coloring agents, buffers, surface active agents such as sorbitan monooleate polyoxyethylene, additional antibacterial agents, astringents, and water may also be used.

Examples of suitable flavoring agents for use in the mouthwashes of the present invention include heliotropyl nitrile, oil of spearmint, wintergreen oil (methyl salicylate), oil of peppermint, and mixtures thereof. Said flavoring agents are generally present in amounts of from about 0.001% to about 1.0%.

Examples of optional antibacterial agents are chlorhexdine, cetyl pyridinium chloride and domiphen bromide which are generally used in amounts of from about 0.01% to about 0.10%.

The aforesaid mouthwash compositions can also be administered in vaporizer or aerosol forms. When administered in aerosol forms, commonly available propellants such as hydrocarbons and fluorohalogen derivatives, for example, dichlorotetrafluoroethane, octafluorocyclobutane, dichlorodifluoromethane, and tetrafluorodichloroethane can be used.

The above mouthwash compositions can also be prepared in a concentrated form for use as a mouthspray.

Method of Manufacture

The compositions of the present invention can be prepared using conventional methods well known and accepted in the oral composition field.

Industrial Applicability

The compositions of the present invention are useful in the oral hygiene area. The dentrifrices and mouthwashes are used in the usual manner.

The following examples further describe and demonstrate the preferred embodiments within the scope of the present invention. Said examples are given solely for the purpose of illustration and are not to be construed as limitations of this invention, as many variations thereof are possible without departing from the spirit and scope thereof. Unless otherwise indicated, all percentages herein are by weight.

EXAMPLE I

A toothpaste having the following composition is prepared utilizing conventional methods.

| Ingredient | Percent by Weight |
| --- | --- |
| Calcium pyrophosphate | 40.00 |
| Sorbitol (70% aqueous solution) | 20.40 |
| Glycerine | 10.20 |
| Sodium coconut monoglyceride sulfonate | 0.82 |
| Sodium lauryl sulfate | 0.80 |
| Sodium carboxymethyl cellulose | 1.00 |
| Magnesium aluminum silicate | 0.40 |
| Stannous fluoride | 0.40 |
| Flavor (spearmint) | 0.90 |
| Color | 0.05 |
| Sweetener (potassium salt of 6-methyl-oxathiazinone dioxide) | 0.55 |
| Water and minors | balance |

The composition of this invention, when used as intended, is an effective dentifrice formulation possessing highly desirable sweetness and stability characteristics.

Toothpaste compositions are prepared in accordance with Example I except that calcium carbonate, dicalcium orthophosphate dihydrate, calcium polymetaphosphate, silica xerogels as disclosed in U.S. Pat. No. 3,538,230, insoluble sodium polymetaphosphate, resinous abrasive materials such as particulate condensation products of urea and formaldehyde as disclosed by Cooley et al in U.S. Pat. No. 3,070,510, zirconium silicate compositions as disclosed by Muhler in U.S. Pat. No. 3,450,813, hydrated alumina, and synthetic amorphous silicas are used, respectively, in place of calcium pyrophosphate. The result in each instance is a desirable toothpaste composition possessing pleasing sweetness characteristics.

Compositions are prepared as in Example I, except that stannous fluoride is replaced by an equivalent amount of sodium fluoride, lithium fluoride, potassium fluoride, ammonium fluoride, stannous chlorofluoride, sodium monofluorophosphate, indium fluoride, and sodium hexafluorantimonate, respectively. The result in each instance is an effective toothpaste composition having pleasing sweetness characteristics.

A toothpaste composition is prepared as in Example I which contains in addition about 1.0% of ethane-1-hydroxy-1,1-diphosphonic acid (EHDP). The result is a dentifrice formulation having desirable sweetness characteristics and calculus inhibiting properties.

EXAMPLE II

A toothpaste composition is prepared having the following formulation:

| Ingredient | Percent by Weight |
| --- | --- |
| Calcium pyrophosphate | 40.00 |
| Sorbitol (70% aqueous solution) | 20.40 |
| Glycerine | 10.20 |
| Sodium coconut monoglyceride sulfonate | 0.80 |
| Sodium carboxymethyl celluose | 1.20 |
| Sodium coconut alkyl sulfate (20% active) | 2.30 |
| Sodium fluoride | 0.22 |
| Sweetener (sodium salt of 6-methyloxathiazinone dioxide) | 0.60 |
| Flavor (peppermint) | 0.90 |
| Green urea formaldehyde agglomerates | 0.65 |
| Water and minors | balance |

The toothpaste of this example exhibits good efficacy while possessing highly desirable sweetness, flavor and stability characteristics.

Toothpaste compositions are prepared in accordance with Example II except that calcium carbonate, dicalcium orthophosphate dihydrate, calcium polymetaphosphate, silica xerogels as disclosed in U.S. Pat. No. 3,538,230, insoluble sodium polymetaphosphate, resinous abrasive materials such as particulate condensation products of urea and formaldehyde as disclosed by Cooley et al in U.S. Pat. No. 3,070,510, zirconium silicate compositions as disclosed in U.S. Pat. No. 3,450,813 hydrated alumina, and synthetic amorphous silicas are used, respectively, in place of calcium pyrophosphate. The result in each instance is a desirable toothpaste composition possessing pleasing sweetness characteristics.

Compositions are prepared as in Example II, except that sodium fluoride is replaced by an equivalent amount of stannous fluoride, lithium fluoride, potassium fluoride, ammonium fluoride, stannous chlorofluoride, sodium monofluorophosphate, indium fluoride, and sodium hexafluoroantimonate, respectively. The result in each instance is an effective toothpaste composition having pleasing sweetness characteristics.

EXAMPLE III

A dentifrice is prepared by conventional means having the following formula:

| Ingredient | Percent by Weight |
| --- | --- |
| Silica xerogel | 12.00 |
| Silica aerogel | 5.00 |
| Hydroxyethyl cellulose | 1.50 |
| Glycerine | 34.76 |
| Stannous fluoride | 0.41 |
| Flavor (wintergreen) | 0.95 |
| Color (FD&C Blue #1) | 0.03 |
| 21% sodium lauryl sulfate-79% glycerine mixture | 6.00 |
| Sweetener (potassium salt of 6-methyl-oxathiazinone dioxide) | 0.40 |
| Water and minors | balance |

The above composition is a stable, effective, translucent dentifrice having desirable sweetness characteristics.

Compositions are prepared as in Example III except that stannous fluoride is replaced by an equivalent amount of sodium fluoride, lithium fluoride, potassium fluoride, ammonium fluoride, stannous chlorofluoride, sodium monofluorophosphate, indium fluoride, and sodium hexafluoroantimonate, respectively. The result in each instance is an effective toothpaste composition having pleasing sweetness characteristics.

EXAMPLE IV

A mouthwash is prepared having the following formulation:

| Ingredient | Percent by Weight |
| --- | --- |
| Glycerine | 10.00 |
| Ethyl alcohol | 17.00 |
| Cetyl pyridinium chloride | 0.05 |
| Sorbitan monooleate polyoxyethylene | 0.13 |
| Flavor (wintergreen) | 0.09 |
| Sweetener (potassium salt of 6-methyl-oxathiazinone dioxide) | 0.11 |
| Water and minors | balance |

The above composition possesses highly desirable mouth freshening characteristics and possesses desirable sweetness characteristics as well.

A composition is prepared substantially in accordance with Example IV, except that the cetyl pyridinium chloride is replaced by chlorhexidine, domiphen bromide and mixtures thereof. The result is a desirable mouthwash having favorable sweetness characteristics.

Compositions in accordance with Example IV are prepared except that the wintergreen oil therein is replaced by oil of peppermint, oil of spearmint and mixtures thereof. In each instance, a desirable mouthwash having most favorable sweetness and flavor characteristics results.

What is claimed is:

1. A toothpaste consisting essentially of:
   (A) from about 0.05% to about 0.80% by weight of 6-methyloxathiazinone dioxide or an alkali metal or alkaline earth salt thereof as a sweetening agent;
   (B) from about 0.5% to about 95% by weight of an abrasive material;
   (C) from about 0.5% to about 5.0% of a sudsing agent;
   (D) from about 0.1% to about 5.0% of a binder material;
   (E) up to about 50% of a humectant material;
   (F) from about 0.01% to about 1.0% of a water-soluble fluorine-containing compound; and
   (G) balance, water and minors.
   (B) from about 0.5% to about 95% by weight of an abrasive material;

2. The toothpaste composition of claim 1 wherein the 6-methyloxathiazinone dioxide salt is a potassium salt and is present in an amount of from about 0.3% to about 0.6%.

3. The toothpaste composition of claim 1 wherein the abrasive material is selected from the group consisting of calcium pyrophosphate, silica xerogels, silica aerogels and mixtures thereof.

4. The toothpaste composition of claim 3 wherein the abrasive is calcium pyrophosphate present in an amount of from about 10% to about 60% by weight.

5. The toothpaste composition of claim 3 wherein the abrasive is a silica xerogel present in an amount of from about 10% to about 60% by weight.

6. The toothpaste composition of claim 1 wherein the sudsing agent is selected from the group consisting of sodium lauryl sulfate, sodium coconut monoglyceride sulfonate, and mixtures thereof.

7. The toothpaste composition of claim 1 wherein the binder is selected from the group consisting of sodium carboxymethyl cellulose, magnesium aluminum silicate, hydroxyethyl cellulose, Irish moss, xantham gum and mixtures thereof.

8. A mouthwash consisting essentially of:
(A) from about 0.05% to about 0.80% by weight of 6-methyloxathiazinone dioxide or an alkali metal or alkaline earth salt thereof as a sweetening agent;
(B) from about 5% to about 60% of ethyl alcohol;
(C) from about 5% to about 20% of a humectant;
(D) from about 0.01% to about 1% of a water soluble fluorine-containing compound; and
(E) balance, water and minor.

9. The mouthwash composition of claim 8 wherein the 6-methyloxathiazinone dioxide salt is a potassium salt and is present in an amount of from about 0.075% to about 0.15%.

10. The mouthwash composition of claim 8 wherein the humectant is glycerine.

* * * * *

UNITED STATES PATENT OFFICE
CERTIFICATE OF CORRECTION

PATENT NO. : 4,256,730

DATED : March 17, 1981

INVENTOR(S) : James J. Benedict

It is certified that error appears in the above-identified patent and that said Letters Patent are hereby corrected as shown below:

Column 2, line 55, "and" should read --are--.

Column 8, lines 61 and 62, "(B) from about 0.5% to about 95% by weight of an abrasive material;" should be deleted.

Column 10, line 11, "minor" should read --minors--.

Signed and Sealed this

Seventh Day of July 1981

[SEAL]

Attest:

RENE D. TEGTMEYER

Attesting Officer

Acting Commissioner of Patents and Trademarks